US009743843B2

(12) United States Patent
Chamney et al.

(10) Patent No.: US 9,743,843 B2
(45) Date of Patent: Aug. 29, 2017

(54) PATIENT SUPPORTING DEVICE, TREATMENT APPARATUS WITH A PATIENT SUPPORTING DEVICE AND CORRESPONDING METHOD FOR CONTROLLING AND/OR REGULATING A MEDICAL TREATMENT DEVICE

(75) Inventors: Paul Chamney, Herts (GB); Peter Wabel, Darmstadt (DE); Ulrich Moissl, Karben (DE); Sebastian Wieskotten, Ober-Ramstadt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1122 days.

(21) Appl. No.: 13/810,771

(22) PCT Filed: Jul. 19, 2011

(86) PCT No.: PCT/EP2011/062330
§ 371 (c)(1),
(2), (4) Date: Mar. 28, 2013

(87) PCT Pub. No.: WO2012/010588
PCT Pub. Date: Jan. 26, 2012

(65) Prior Publication Data
US 2013/0204098 A1  Aug. 8, 2013

(30) Foreign Application Priority Data
Jul. 19, 2010  (DE) .................... 10 2010 031 530

(51) Int. Cl.
*A61B 5/053* (2006.01)
*A61B 5/0205* (2006.01)
(Continued)

(52) U.S. Cl.
CPC ........ *A61B 5/0205* (2013.01); *A61B 5/04005* (2013.01); *A61B 5/0537* (2013.01);
(Continued)

(58) Field of Classification Search
CPC . A61B 5/0205; A61B 5/04005; A61B 5/0537; A61B 5/1073; A61B 5/4836;
(Continued)

(56) References Cited

U.S. PATENT DOCUMENTS 3,482,573 A   12/1969  Stoever
5,771,511 A    6/1998  Kummer et al.
(Continued)

FOREIGN PATENT DOCUMENTS

CH    469 490      4/1969
DE   22 24 659   11/1972
(Continued)

OTHER PUBLICATIONS

Grimnes: Bioelectricity and Bioimpedance Basics. Academic Press 2008.
(Continued)

*Primary Examiner* — Adam J Eiseman
(74) *Attorney, Agent, or Firm* — Jacobson Holman, PLLC.

(57) ABSTRACT

The subject matter is a patient supporting device for supporting a patient during a medical treatment, in particular a dialysis treatment, and a treatment apparatus with such a patient supporting device, and a corresponding method for controlling and/or regulating a medical treatment device, in particular a dialysis device, using such a patient supporting device.

16 Claims, 4 Drawing Sheets

(51) Int. Cl.
*A61B 5/1172* (2016.01)
*A61B 5/00* (2006.01)
*A61G 15/02* (2006.01)
*A61M 1/14* (2006.01)
*A61B 5/04* (2006.01)
*A61B 5/107* (2006.01)
*A61B 5/145* (2006.01)
*A61B 5/1455* (2006.01)
*A61B 5/1468* (2006.01)
*A61B 7/00* (2006.01)
*A61M 1/16* (2006.01)
*A61G 7/075* (2006.01)
*A61G 15/12* (2006.01)

(52) U.S. Cl.
CPC .......... *A61B 5/1072* (2013.01); *A61B 5/1073* (2013.01); *A61B 5/1079* (2013.01); *A61B 5/1172* (2013.01); *A61B 5/1455* (2013.01); *A61B 5/1468* (2013.01); *A61B 5/14532* (2013.01); *A61B 5/14546* (2013.01); *A61B 5/4836* (2013.01); *A61B 5/4869* (2013.01); *A61B 5/6887* (2013.01); *A61B 5/70* (2013.01); *A61B 7/00* (2013.01); *A61G 15/02* (2013.01); *A61M 1/14* (2013.01); *A61M 1/1611* (2014.02); *A61B 5/6891* (2013.01); *A61G 7/075* (2013.01); *A61G 15/12* (2013.01); *A61G 2210/00* (2013.01); *A61G 2210/20* (2013.01); *A61M 2230/65* (2013.01)

(58) Field of Classification Search
CPC ... A61B 5/4869; A61B 5/6887; A61B 5/6891; A61B 5/6892; A61B 5/6894
See application file for complete search history.

(56) References Cited

U.S. PATENT DOCUMENTS

| | | | |
|---|---|---|---|
| 6,327,494 B1 | 12/2001 | Sakai | |
| 6,585,328 B1 * | 7/2003 | Oexman | A47C 31/123 5/706 |
| 7,172,569 B2 | 2/2007 | Kleinekofort | |
| 7,801,598 B2 | 9/2010 | Zhu et al. | |
| 2002/0054299 A1 * | 5/2002 | Freifeld | G01B 11/024 356/625 |
| 2003/0216665 A1 | 11/2003 | Masuo et al. | |
| 2004/0059242 A1 | 3/2004 | Masuo et al. | |
| 2004/0073123 A1 * | 4/2004 | Hessel | A61B 5/021 600/490 |
| 2004/0167423 A1 | 8/2004 | Pillon et al. | |
| 2005/0102165 A1 | 5/2005 | Oshita et al. | |
| 2005/0278197 A1 * | 12/2005 | Podczerwinski | G06Q 50/24 705/3 |
| 2008/0221474 A1 | 9/2008 | Waffenschmidt et al. | |
| 2009/0043222 A1 | 2/2009 | Chetham | |
| 2009/0275808 A1 | 11/2009 | DiMaio et al. | |
| 2009/0292236 A1 | 11/2009 | Kleinekofort | |
| 2010/0100003 A1 | 4/2010 | Chetham et al. | |
| 2010/0168530 A1 | 7/2010 | Chetham et al. | |
| 2013/0134077 A1 | 5/2013 | Wieskotten et al. | |

FOREIGN PATENT DOCUMENTS

| | | |
|---|---|---|
| DE | 295 01 201 | 5/1995 |
| DE | 299 15 914 | 1/2000 |
| DE | 200 18 409 | 2/2002 |
| DE | 101 41 053 | 1/2006 |
| DE | 699 23 520 | 3/2006 |
| DE | 10 2006 032815 | 1/2008 |
| DE | 601 32 033 | 12/2008 |
| DE | 10 2008 012989 | 5/2009 |
| DE | 10 2010 028 902 | 11/2011 |
| EP | 1 645 227 | 12/2007 |
| JP | 10-085326 | 4/1998 |
| WO | WO 2006/111878 | 10/2006 |
| WO | WO 2007/090119 | 8/2007 |

OTHER PUBLICATIONS

Moissl et al. Body fluid volume determination via body composition spectroscopy in health and disease. Physiological Measurement. 27 (2006) 921-933.

CHAMNEYe t al. A whole-body model to distinguish excess fluid from the hydration fo major body tissues. Am J. Clin Nutr 2007;85:80-9.

* cited by examiner ated method for controlling and/or regulating a dialysis device, which do not have these disadvantages, but use the advantages of bioimpedance measurement, or similar measurement methods, for monitoring and controlling a dialysis treatment.

PATIENT SUPPORTING DEVICE, TREATMENT APPARATUS WITH A PATIENT SUPPORTING DEVICE AND CORRESPONDING METHOD FOR CONTROLLING AND/OR REGULATING A MEDICAL TREATMENT DEVICE

This is a national stage of PCT/EP11/062330 filed Jul. 19, 2011 and published in German, which has a priority of German no. 10 2010 031 530.3 filed Jul. 19, 2010, hereby incorporated by reference.

FIELD OF THE INVENTION

The invention relates to a patient supporting device for supporting a patient during a medical dialysis treatment, and to a treatment apparatus with such a patient supporting device, and to a corresponding method for controlling and/or regulating a dialysis device using such a patient supporting device.

PRIOR ART

Dialysis is a method of purifying blood, which among other uses is employed as a replacement therapy in cases of renal failure, in which mass transfer takes place through a semipermeable membrane, which is in contact on one side with the patient's blood and on the other with a dialysis solution (dialysate). This is intended to remove undesirable substances such as pyrogens, noxa, certain metabolites, and also excess water from the patient's blood by ultrafiltration.

Such dialysis treatments can last for several hours, with the patient obliged to remain motionless, or make only minor movements (i.e. sit or lie) during the treatment. Therefore it has long been usual in the prior art to employ dialysis chairs, armchairs or couches as patient supporting devices, which enable the patient to remain in a comfortable posture even during dialysis treatment which lasts several hours. Nowadays, however, the usual preferred supporting devices are patient couches, one of the reasons being that they offer more comfort than chairs. In these patient couches, the patient support surface is generally adjustable to a plurality of positions and enables the patient to adopt both sitting and lying positions. The patient can thereby be in a relatively comfortable sitting or lying position during the dialysis treatment, which, for example in the case of hemodialysis treatment, can last for several hours. At the same time, such a couch enables the patient to be positioned in such a way that he or she is less susceptible to circulation problems during extracorporeal blood treatments, which inherently place demands on the patients' blood circulation.

DE 299 15 914 U1 describes a treatment couch with a patient support surface which is divided into three support areas, with at least one support area having an element for generating vibrations to stimulate the patient's circulation. JP 10085326 A describes a patient couch within which a hemodialysis device is integrated. DE 101 41 053 B4 also discloses a patient couch which has an extracorporeal blood treatment device as an integral part. CH 469 490 proposes a chair within which parts of a hemodialysis apparatus are disposed. U.S. Pat. No. 5,771,511 has as its subject-matter a hospital bed with modules which are integrated in a communication network.

In such a dialysis treatment, the monitoring of the hydration status of the patient during the dialysis procedure is a vital factor in the success of the dialysis and the welfare and health of the patient.

For this purpose, bioimpedance measurement is increasingly used to determine the patient's water content and for support during the dialysis treatment (i.e. in particular to determine the parameters of the dialysis therapy and to monitor the success of the treatment). Bioimpedance measurement, often also carried out in the form of bioimpedance spectroscopy or bioimpedance vector analysis, is a method which is for the most part used non-invasively for determining the intracellular and extracellular volumes of fluids. In this method, body impedances, i.e. alternating current resistances of body tissues, are measured by means of electrodes attached to the surface of the patient's skin (stimulation electrodes=coupling-in electrodes; discharge electrodes=coupling-out electrodes). The analysis can take into account phase displacements and frequency-dependent variations in the impedance.

The prior art already uses, for example, a commercially available Body Composition Monitor from Fresenius Medical Care AG & Co. KGaA, 61346 Bad Homburg v.d.H., Germany, in order to check the water content in the patient's body composition by means of bioimpedance measurement and use this to monitor and control the dialysis device. For this purpose electrodes are attached to one of the patient's hands and one foot, and the electrodes are connected by a cable to the measuring device, enabling the data collected to be used offline (e.g. for follow-up medical examinations) or online, for instance to control the dialysis device. Another example of the use of bioimpedance measurement to determine a dialysis patient's hydration status, and to monitor a dialysis device, is described in EP 1 645 227 B1, which outlines a method for determining a patient's hydration status by bioimpedance measurement, also using electrodes attached to a patient's limb.

Because the bioimpedance measurement is influenced by body posture, it is advisable to carry out the measurement primarily when the patient is lying down, since this enables the body posture to be reproduced most accurately. However, the prior art also proposes devices for measurement in a sitting position. US 2004/0059242 A1, for example, discloses on page 31 [Fifth Embodiment] a chair with integrated electrodes for determining body composition.

The measurement can usually take place before and/or after the treatment, in order to determine the hydration status prior to the dialysis and use this knowledge to set treatment options (ultrafiltration quantity and rate, length of dialysis, filter type, blood flow, dialysate flow, dialysate composition etc.), and/or after the treatment to examine the success of the therapy with respect to water removal. The methods known in the prior art have in common that they entail relatively high personnel costs due to the necessity for highly-qualified staff. Moreover, most of the prior art devices and methods are not yet satisfactory under all conditions with regard to accuracy of measurement and/or susceptibility to interference. To some extent this can lead to measurement errors, for example with patients having special clinical pictures or exceptional deviations in physiological parameters. There is also the possibility of operating errors on the part of staff when applying the bioimpedance measurement electrodes and connecting them to cables, and/or when recording and transmitting the patient data that is required for the correct evaluation of the bioimpedance measurement.

DISCLOSURE OF THE INVENTION

The object of the present invention is to provide a patient supporting device and a corresponding treatment apparatus with a patient supporting device and a medical treatment device, by means of which handling during a medical treatment is facilitated, the adjustment and checking of the medical treatment device is simplified, and the safety of the treatment for the patient is improved. In addition, a corresponding method is specified, which is based on the same object.

This object is achieved as regards the patient supporting device by the patient supporting device disclosed, and as regards the method by the method disclosed. Furthermore, in order to achieve this object the disclosure specifies a treatment apparatus with a patient supporting device and a medical treatment device, which achieves the object in the same manner. Preferred embodiments are set forth.

According to the present invention, a patient supporting device for positioning a patient is specified, with an apparatus for carrying out a bioimpedance measurement on a patient's body, wherein this apparatus has a device for coupling a measurement signal into the patient's body and a device for coupling an electrical measurement value thereby generated in the patient's body out of the patient's body, and an interface to a medical treatment device, in particular a dialysis device, wherein via this interface the data correlated with the electrical measurement value can be transmitted to the medical treatment device, in particular dialysis device, by means of which the medical treatment device, in particular dialysis device, can be controlled and/or regulated.

The coupling-in and coupling-out of the measurement signal and electrical measurement value respectively can take place by means of direct electrical contact with areas of the patient's skin, or instead by means of capacitive, magnetic and/or electromagnetic coupling-in and coupling-out using capacitor plates, coils or other electromagnetic emitting devices. The apparatus for carrying out a bioimpedance measurement, which is integrated in the patient supporting device, comprises at least the coupling-in and coupling-out devices according to the subject-matter of the claim, preferably with the necessary cabling to an interface for connection to a medical treatment device, in particular a dialysis device. It is possible—and, depending on the requirements of the application, may also be appropriate— that signal generators for generating the measurement signal and/or devices for detection and evaluation of the coupled-out electrical measurement value can also be integrated in the patient supporting device and, for example, calculate bioimpedance at that stage, and pass this via the interface to the medical treatment device, in particular dialysis device, or generate appropriate control signals for the medical treatment device, in particular dialysis device, and transmit these to the device. It is, however, also within the scope of the subject-matter of the invention that at least parts of the above-mentioned processes, such as for example measurement signal generation and evaluation of the electrical measurement value, are carried out in an appropriate processing unit of the medical treatment device, in particular dialysis device, and/or in separate devices. The term "data correlated with the electrical measurement value" is to be understood as all measured values, information and/or data (and thus for example including bioimpedance measurements) which are directly or indirectly obtained (as raw data and/or as the result of a calculation process also taking account of other data) from the electrical measurement value, and/or which relate to the measurement signal on the stimulation side of the bioimpedance measurement. This data contains important physiological and/or pathological information about the patient and/or the dialysis process (including for example the patient's hydration status), and this information can be exchanged via the interface with the medical treatment device, in particular dialysis device, and can be used for example for controlling and/or regulating that device. The individual data preparation and processing steps can be carried out "upstream" and/or "downstream" of the interface, in the patient supporting device, the medical treatment device, in particular dialysis device, and/or in a different device.

In the patient supporting device specified here it is possible to implement the coupling-in and coupling-out devices separately, or to provide combined coupling-in and coupling-out devices. It is preferable to use a measurement signal with at least two, preferably with at least three frequencies, particularly preferably with a continuous frequency spectrum. These frequencies can be applied and measured either consecutively (sequentially), or else simultaneously as a complex periodic signal waveform or as a frequency mixture whose Fourier spectrum contains multiple frequencies.

Furthermore, a corresponding treatment apparatus is disclosed, with a patient supporting device according to one of the previous claims, a medical treatment device, in particular dialysis device, and an evaluation apparatus for evaluating the bioimpedance from the electrical measurement value that is coupled out by the apparatus for carrying out a bioimpedance measurement, wherein the medical treatment device, in particular dialysis device, can be controlled and/or regulated by the bioimpedance.

Finally, a method for controlling and/or regulating a medical treatment device, in particular dialysis device, is specified, having the following steps:

positioning a patient on a supporting surface of a patient supporting device with at least two electrodes for contacting the patient's body for coupling the measurement signal into the patient's body (=coupling-in electrodes), and at least two electrodes for contacting the patient's body for coupling the electrical measurement value generated by the measurement signal in the patient's body out of the patient's body (=coupling-out electrodes), wherein the positioning of the patient takes place such that parts of the surface of the patient's skin make electrical contact with the coupling-in electrodes and coupling-out electrodes, coupling a measurement signal into the patient's body, preferably by impressing a measurement current into the patient's body, coupling an electrical measurement value that is thereby generated in the patient's body out of the patient's body, preferably by capturing a change in potential generated by the measurement signal in the patient's body, detecting the electrical measurement value, determining a bioimpedance using the measured electrical measurement value, using the determined bioimpedance for controlling and/or regulating the medical treatment device, in particular a dialysis device.

The invention will be described below using the example of dialysis therapy and a dialysis device. This does not limit the invention to this application. It is evident to the skilled person that the invention can be used advantageously with a multiplicity of medical treatment devices, e.g. plasmapheresis devices, peritoneal dialysis devices, hemodialysis devices, devices for liver support therapy, devices for cardiovascular system support or therapy, and similar.

The advantages of the method and devices according to the invention are, among others, that handling when carrying out the dialysis therapy is considerably simplified and accelerated, and the incidence of errors (for example due to failure to connect a cable to the patient) is reduced, with the result that staff with lower levels of qualifications can also carry out and monitor the dialysis treatment. At the same time, the danger of incorrect adjustment of the dialysis device is reduced, and the input or transmission of patient data (such as the patient's height and weight, which are required for the correct evaluation of the bioimpedance measurement, as well as the treating physician's treatment recommendations or instructions for setting the parameters of the dialysis device) is simplified or even rendered obsolete.

Reliable, continuous (or quasi-continuous) i.e. intradialytic monitoring, control and/or regulation of the dialysis device is also possible, along with the triggering of an alarm signal if there is a malfunction or particular limit values are exceeded. In addition, the method and devices according to the invention enable more precise detection of the extremely important hydration status of the patient and the dialytic water exchange processes "online", i.e. intradialytically, during the dialysis treatment. The method and devices according to the invention thereby provide immediate evidence of the overall hydration status of the patient, and even, if segmental bioimpedance spectroscopy is used, of individual body segments. Moreover the method proposed here permits, for example, additional checking of the control of the dialysis device and continuous monitoring of the dialysis process.

In addition, with the method and devices according to the invention it is possible to achieve a high degree of accuracy of measurement (by means of, among other factors, the minimization of artifacts and the attainment of high specificity of the analyzed parameters) and/or low susceptibility to interference under almost all conditions, including for example in the case of patients having special clinical pictures or exceptional deviations in physiological parameters.

The measurement signal can be an electrical, magnetic and/or electromagnetic alternating field, wherein the frequency of the alternating field is preferably variable, in particular modulable. By using differing frequencies, preferably through frequency modulation of the alternating field, the complex system can be analyzed according to a plurality of parameters, for example physiological and/or pathological parameters, and it is also possible to carry out impedance spectroscopy, by means of which particularly informative and precise results can be obtained. Alternatively, however, it is also conceivable to use a different type of sequential variation of the frequency of the alternating field (for example abrupt change), or to use a plurality of frequencies simultaneously (for example as a complex periodic signal waveform or as a frequency mixture, whose Fourier spectrum contains multiple frequencies).

Alongside this, it is also possible for the coupling of the electrical measurement signal into the patient's body and/or the coupling-out of the electrical measurement value thereby generated in the patient's body to be carried out capacitively and inductively. By this means the advantages of the two coupling methods can be combined: inductive coupling can advantageously be employed for low frequencies, and capacitive coupling, due to the high-pass characteristics of this coupling method, can advantageously be employed for the higher frequencies. The different coupling methods can be used for measurement simultaneously or successively, wherein it is possible to combine the coupled-in measurement signal and/or the coupled-out electrical measurement value for both coupling methods, or to process them separately. Furthermore, coupling methods of this type may also be suitable in certain circumstances for measurement through the patient's clothing, bringing additional advantages if these methods are used.

It is often advantageous if the determination of the bioimpedance is carried out at a plurality of different frequencies of the electrical measurement signal according to amplitude and phase, preferably with high resolution of the amplitude and phase. In this, a measurement current can for example be impressed into the patient's body by means of a measurement signal which varies over time, and the voltage drop thus produced in the patient's body can be measured. This represents a particularly advantageous measurement procedure, especially in terms of a high degree of accuracy of measurement and reduced susceptibility to interference. The accuracy of measurement can be still further increased by the separate evaluation of amplitude attenuation and phase shift. In order to achieve the greatest possible accuracy of measurement, it is expedient to detect the amplitude attenuation and phase shift of the electrical measurement signal with high temporal resolution. By this means it is also possible to increase still further the specificity of the measurement results. A suitable network analyzer can for example be used for this purpose.

It can also be advantageous for the analysis of the bioimpedance to carry out an evaluation according to the Cole model. The Cole model represents a simple description of the ohmic and capacitive ratios in two-compartment systems, such as for example blood fluids or body tissues, and thereby depicts the electrical ratios in an easily analyzable form with a good level of accuracy.

Because the patient's hydration status is continuously monitored, it is also possible and advantageous to use this parameter, at least as an additional parameter, for controlling and/or regulating the dialysis device, whereby preferably the transmembrane pressure in the dialysis device can be controlled. It is thereby possible to make the desired measurement of the water content directly, and for example adjust this to an optimum value via the control of the dialysis device. The relevant adjustment could be carried out for example by a regulation system via the control of the blood pump, dialysate pump or ultrafiltration pump of the dialysis device (via their influence on the transmembrane pressure in the dialysis cell) by means of direct feedback of the variable to be regulated (namely the water content).

In a preferred embodiment, the apparatus for carrying out a bioimpedance measurement can have a device for determining the patient's weight. Because the patient's weight forms a part of the bioimpedance calculation, and undergoes certain fluctuations which are of significance for the carrying out and the evaluation of the bioimpedance measurement, it is essential to determine the patient's weight prior to the bioimpedance measurement. By equipping the patient supporting device with a weighing device whose data is integrally linked to the apparatus for carrying out a bioimpedance measurement, this measurement can be automated and directly incorporated in the calculation of the bioimpedance. In particular, the variations in weight caused by the removal of excess water from the patient's body during dialysis can also be taken into account. Thus it is possible to dispense with a separate weighing of the patient and transmission of the measured weight to the dialysis device, reducing significantly the work required and the sources of error. Moreover, the change in the patient's weight provides a valuable indication of the water removal that has taken place, and this can be used for controlling and/or regulating the dialysis device.

In a further preferred embodiment, the apparatus for carrying out a bioimpedance measurement can have at least two electrodes for contacting the patient's body for coupling the measurement signal into the patient's body (=coupling-in electrodes), preferably by impressing a measurement current into the patient's body, and at least two electrodes for contacting the patient's body for coupling the electrical measurement value generated by the measurement signal in the patient's body out of the patient's body (=coupling-out electrodes), preferably by capturing a change in potential generated by the measurement signal in the patient's body. This allows the electrical quantities to be coupled in and coupled out in a particularly simple manner. By the use of separate coupling-in electrodes and coupling-out electrodes, the bioimpedance measurement can be carried out as four-point measurement, enabling a considerable increase in the accuracy of measurement. It is particularly advantageous to impress the measurement signal as a current signal, and capture the change in potential caused by the impressing of the measurement signal by means of a high impedance signal follower.

In a further preferred embodiment, the apparatus for carrying out a bioimpedance measurement can have a plurality of coupling-in electrodes and coupling-out electrodes, preferably at least one coupling-in electrode in each case and at least one coupling-out electrode in each case for contacting each arm and each leg of the patient, preferably for carrying out a segmental bioimpedance measurement. This possesses the advantage that the bioimpedance measurement can be carried out selectively for individual portions of the body, enabling more informative evaluations at the level of individual body segments. This embodiment also provides redundancy in the detection of the electrical measurement value, which reduces susceptibility to interference and enables greater accuracy of measurement to be achieved. Thus it is possible, for example, to carry out separate bioimpedance measurement for the arm of the patient which is connected to the extracorporeal dialysis circulation, or to carry out a right/left comparison between the patient's two arms. This comparison can be used, for example with long-term monitoring over a plurality of hemodialysis treatments, of the segmental bioimpedance of the arm which contains the punctured fistula, in order to monitor the condition of the fistula, for example for a stenosis. Because a large portion of the injected measurement current in this arm flows through the blood, the bioimpedance of the blood increases if there is reduced blood flow in the fistula due to a developing stenosis. This increase in bioimpedance can be detected by longer-term monitoring and evaluation of the segmental bioimpedance of the arm with the punctured fistula over a plurality of hemodialysis treatments.

In addition, the formation of stenoses can be detected at an early stage by means of this arrangement. It is also possible to detect the distribution of water and changes in this during the dialysis, and thereby for example monitor the removal of water from legs, thorax and/or abdomen through the change in the measurable excess water in the respective body segments. For this purpose the coupling-in electrodes and coupling-out electrodes can be disposed for example in the area of the heel support for the patient's right and left legs, and in the terminal forearm area near the carpal bones of the patient's right and left arms, in the patient support area on the patient supporting device. In this it is advantageous if the coupling-in electrodes are disposed distally of the coupling-out electrodes, in order thereby to implement the "four-point measurement" principle. It is however also conceivable to increase the number of measurement points (=coupling-in electrodes) and dispose these additionally in the patient's calf area, lumbar region, neck area and elbow area in the patient support area on the patient supporting device—in the case of electrodes disposed laterally to the sagittal plane, in each case symmetrically in pairs for both halves of the body. This enables highly accurate analysis of the different body segments with at the same time simple and reliable contacts.

In a further preferred embodiment the bioimpedance measurement can be bioimpedance spectroscopy and/or bioimpedance vector analysis, preferably with selective detection of amplitude variation and phase displacement in the electrical measurement value, particularly preferably at a high resolution. By this means it is possible to achieve a particularly high accuracy of measurement and specificity of the measurement results in the detection of the various physiological and/or pathological parameters.

In a further preferred embodiment the bioimpedance measurement can comprise a linear and a non-linear analysis of the electrical measurement value. By means of additional measurement, for example of transient response, "white noise" analyses, or the dynamic pulse response of the tissue areas that are measured in the patient, it is possible to carry out additional detailed analyses, and reliably detect or quantify a multiplicity of physiological and/or pathological parameters simultaneously.

In a further preferred embodiment it can be possible to evaluate the measurement value of the bioimpedance measurement in the patients body together with a measurement value of a blood analysis in an extracorporeal circulation of the dialysis device. By linking the bioimpedance measurements in the patients body with appropriate analyses of the blood in the extracorporeal circulation of the dialysis device before and after the dialysis filter, it is possible to gain a great deal of additional information. Thus it is possible to effect changes in the intracellular and/or extracellular components of the composition of the blood, and correlate these with the measured bioimpedance values from the patient's body. In this the blood analysis can comprise any type of analysis of blood, e.g. determination of glucose, sodium, hemoglobin, urea or albumin, using any types of sensors, such as optical, acoustic or electrical sensor devices, in particular bioimpedance measurement.

In a further preferred embodiment the patient supporting device can have a device for determining the patient's height, preferably with sensors and/or sensor arrays, in particular pressure sensors and/or pressure sensor arrays, which are preferably disposed in the area of patient supporting surfaces of the patient supporting device. The information on the patient's height which is required for the evaluation of the bioimpedance measurement can advantageously also be determined automatically, for example by means of pressure, contact and/or proximity sensors. It is also conceivable to use ultrasonic or laser measuring devices for this purpose, to measure the distance to, for example, the soles of the feet and the crown of the head, and thereby determine the length of the patient's body.

For determining the patient's height, the patient supporting device can also comprise sensors which determine the position of a foot rest attached to the patient supporting device. It has been shown that the position of the foot rest correlates well with the patient's body height, so that the height can be derived from the known position of the foot rest.

In a further preferred embodiment the patient supporting device can have an optical measurement device for the preferably multi-dimensional, in particular three-dimensional detection of the patient's measurements. For this purpose, for example, one or a plurality of laser scanners, cameras and/or 3D scanners can be employed, in order to determine for example the body height or other important body measurements, establish a three-dimensional profile of the body for example in the sagittal plane (e.g. to improve the accuracy of the measurement of hydrostatic pressure, as described below), or produce three-dimensional models of the surface of the body, for example in order additionally to detect possible breathing or movement artifacts in the measurements, or changes in volume (e.g. of the legs and/or abdomen) caused by the dialytic water removal.

In a further preferred embodiment the patient supporting device can have an apparatus for the detection and/or calculation of the hydrostatic pressure at least by the use of position adjustment parameters of the patient supporting device, in particular the inclination of the back rest and/or the foot rest. In the prior art, methods for measuring the arterial flow are described. For this purpose, U.S. Pat. No. 7,172,569, for example discloses a method that measures the venous and arterial pressure while the blood flow is varied. In this case, it is important that the patient does not change position during the measurement, since the arm position in particular directly affects the pressure signals. If the position of the back rest is now known from the recline setting of the patient supporting device, and if it is furthermore ensured by the reliable measurement of the segmental bioimpedance that the arm is in fact resting on this rest, it is possible thereby to estimate the hydrostatic pressure. The accuracy of this estimation can be considerably further improved if it is combined with the above-mentioned multi-dimensional detection of the measurements of the patient's body.

In a further preferred embodiment the patient supporting device can comprise an apparatus for detecting the positions of the arm rests. In order to determine the blood pressure in the patient's fistula, the dialysis machine can be equipped with a pressure sensor. This pressure sensor can, however, determine only the pressure in the blood tube to the fistula. The difference in hydrostatic pressure between the elevation of the pressure sensor in the dialysis machine and the elevation of the patient's arm plays a part in the calculation of the pressure in the fistula. Through knowledge of the position of the patient's arm, in particular its height above the ground, the elevation of the fistula can be determined to a large extent, and the difference in hydrostatic pressure can thereby be determined.

In a further preferred embodiment the patient supporting device can have a motor-driven adjusting device preferably for at least the back rest and/or foot rest. A motor-driven adjusting device which can be controlled by the dialysis device is particularly preferable.

By this means, firstly, the patient's body can be positioned in a way which is both comfortable and advantageous for the dialysis and the planned measurements. In addition, it is possible to adjust the device to a position in which the patient is less susceptible to circulation problems during extracorporeal blood treatments, which inherently put stress on the patients' blood circulation, or if necessary to counteract a critical condition of the patient's circulation. It is also known from the prior art that the patient's posture, or the position of the patient on the patient supporting device, influences the bioimpedance measurement. By means of the motor-driven adjustability of the patient supporting device, on the one hand it is possible to evaluate the influence of the patient's position, which is then substantially known (the patient can be actively "forced" into the body positions by adjustment of the rests), and on the other hand the body position, which is known from the adjustment of the patient supporting device, can be incorporated in the determination of the bioimpedance. The motor-driven adjustability can further be used to evaluate and influence the orthostatic regulation of the patient's circulation, and also to improve the measurement of the hydrostatic pressure, by adjusting the positions of the back rest, foot rest and arm rests to optimum positions during this measurement, or by carrying out the measurement of the hydrostatic pressure in different positions, thereby enabling the accuracy of the measurement of the hydrostatic pressure to be further increased. Furthermore, the condition of the patient can be monitored, for example by the dialysis device. If a patient collapse is detected, or the patient's circulation parameters approach, or threaten to approach, critical values, the dialysis device can control the motor-driven adjusting device of the patient supporting device such that the patient is brought into a shock position, for example into the Trendelenburg position.

In a further preferred embodiment the patient supporting device can have a device for determining the patient's identity, preferably using a fingerprint sensor. This can take place for example by the insertion of a patient card (for example a smart card with a storage chip from the treatment facility, a chip card from the medical insurer, or an RFID card), or else for example using a barcode on a patient's record card. However, for this purpose it is advantageous to use a fingerprint sensor, for example integrated in the arm rest of the patient supporting device. By means of such a sensor the patient can be unambiguously identified, and a stored data set for this individual patient can thereby be reliably accessed. This data set can for example be stored in the dialysis device itself, or advantageously kept on a networked server.

The invention is not limited by the particular embodiments; the features of all of the above-mentioned embodiments can be freely combined with each other, if and to the extent that they are not mutually exclusive for technical reasons and do not have negative effects on each other.

DESCRIPTION OF THE FIGURES

Two example embodiments of the invention are explained in detail below with the aid of the drawings. The drawings show.

As described in detail in the German patent application DE 10 2010 028 902.7, bioimpedance measurement can be carried out in human tissue, and also non-invasively on the patient's body. For this purpose, for example, both a coupling-in electrode and a coupling-out electrode in each case can be connected to the end portions of two extremities (i.e. for example the right arm and left arm, or right leg and left leg, or right arm and right leg). At each of these extremities the coupling-in electrode should be distal of the coupling-out electrode, in order to use the arrangement based on the principle of "four-point measurement". In the following description, "left arm" or "right arm" always includes the hand, and "left leg" or "right leg" always includes the foot.

However, it is particularly advantageous to carry out segmental bioimpedance measurement using eight electrodes, with both coupling-in electrodes and coupling-out electrodes disposed on each of the patient's arms and legs according to the above-mentioned principle. By this means it is possible to determine the bioimpedance of the individual arms and legs, as well as the patient's torso. The principle is explained with the aid of FIG. 1.

The following six measurements are made:
$Z_1$: right side of the body
$Z_2$: left side of the body
$Z_3$: right hand→left foot
$Z_4$: left hand→right foot
$Z_5$: right hand→left hand
$Z_6$: right foot→left foot.

Figure 1:
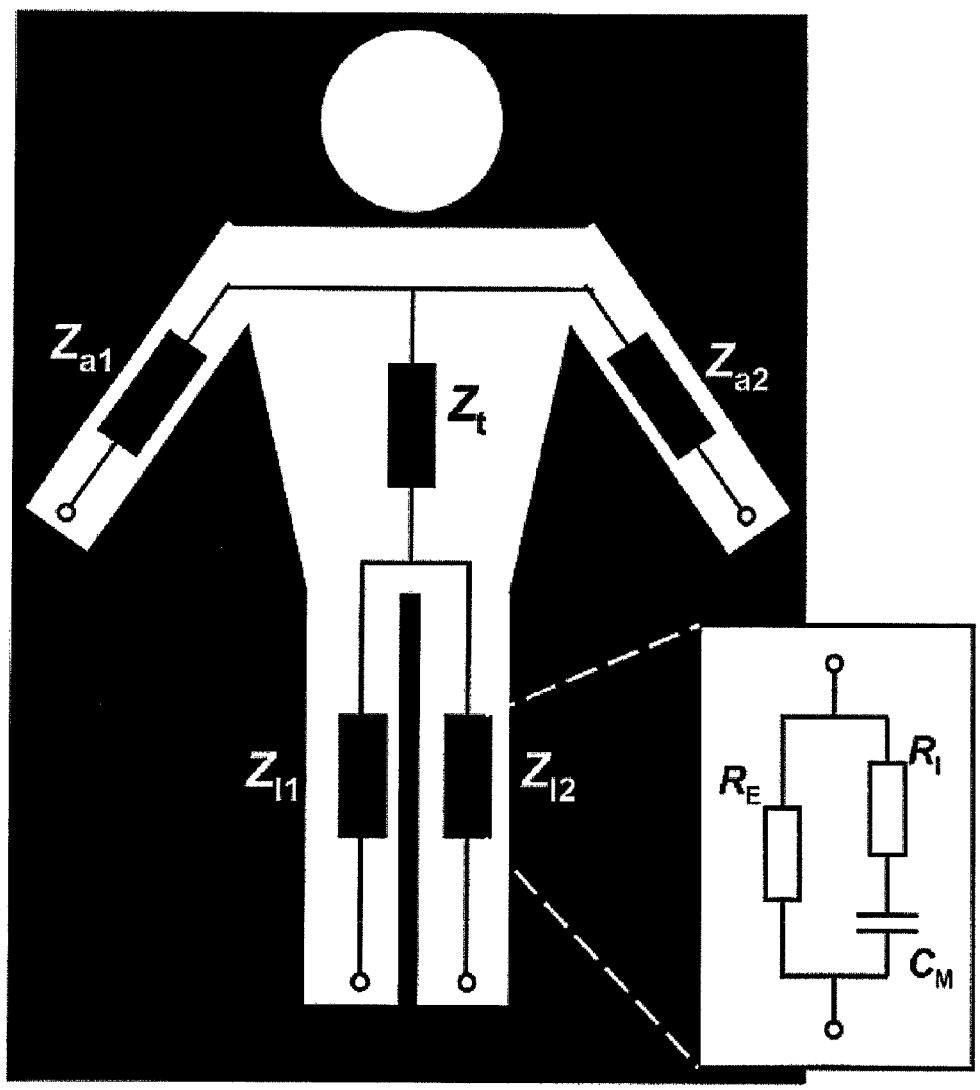
FIG. 1 equivalent circuit diagram for the segmental bioimpedances of the human body.

From these, using the resistor network of the equivalent circuit for the body impedances of the patient shown in FIG. 1, the five segmental bioimpedances can be calculated:
$Z_{a1}$: right arm
$Z_{a2}$: left arm
$Z_t$: torso
$Z_{l1}$: right leg
$Z_{l2}$: left leg.

Figure 2:
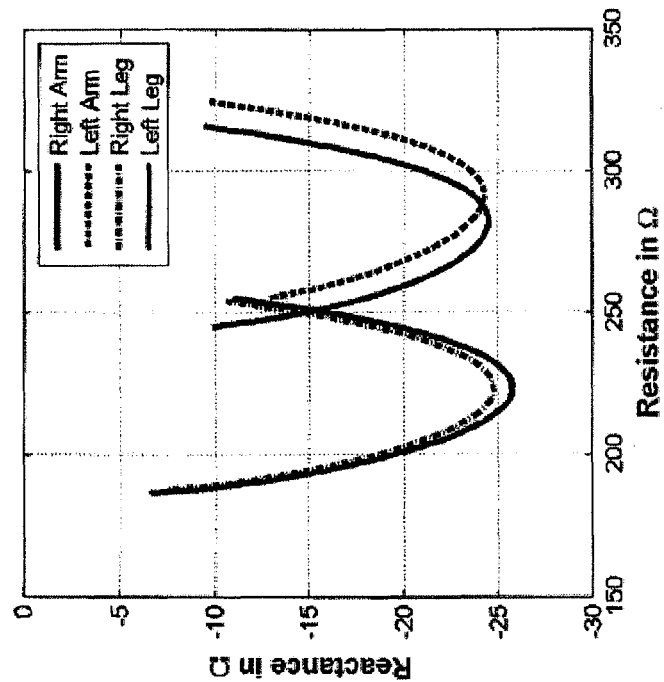
FIG. 2 bioimpedances of the human body (right: measurement curves—left: calculated bioimpedances of the extremities)
Figure 2:
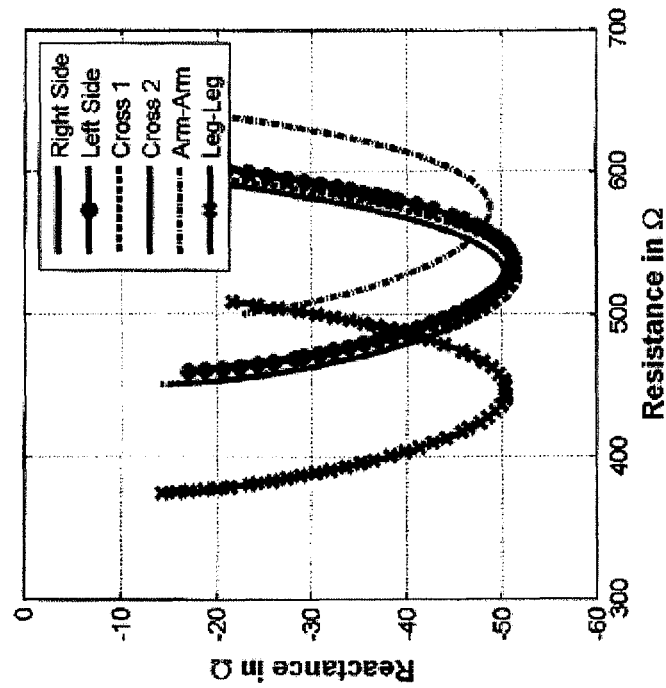
Figure 3:
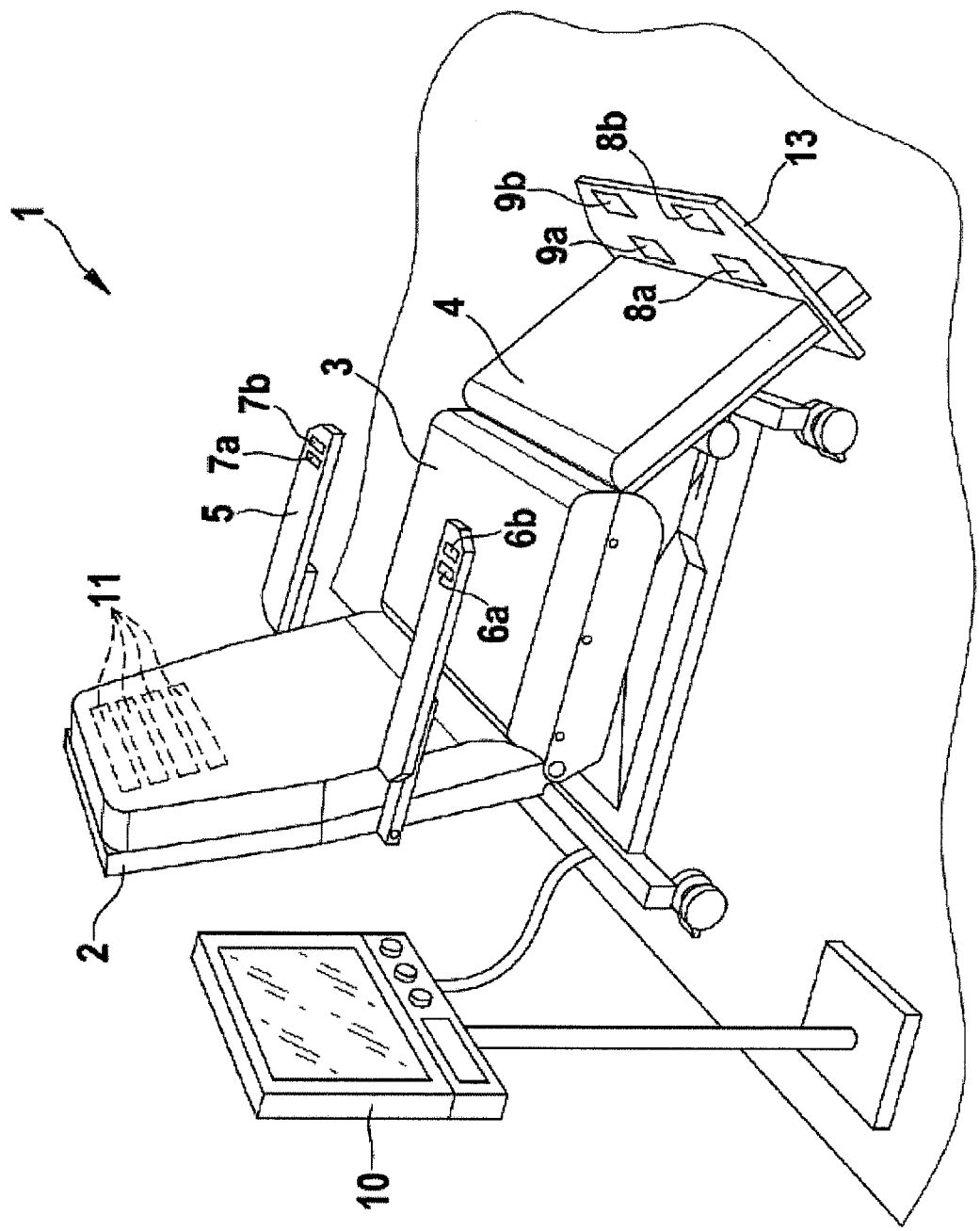
FIG. 3 an embodiment of a patient supporting device according to the invention with a display and operating device for position setting and bioimpedance measurement.
Figure 4:
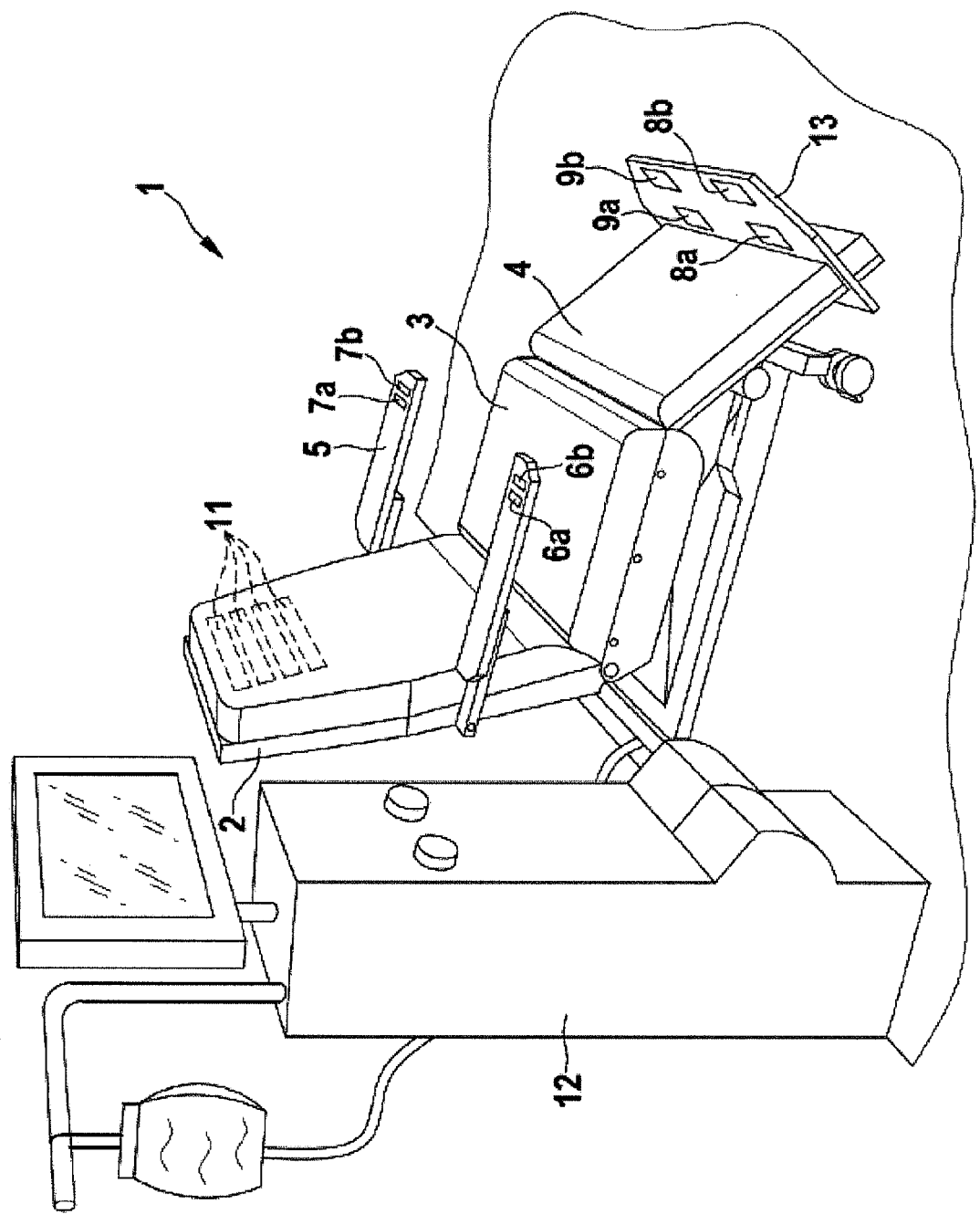
FIG. 4 an embodiment of a patient supporting device according to the invention, which is connected to a dialysis device.

Six measurement curves are thereby obtained for the body impedances from the bioimpedance measurements, as shown in the left hand graph in FIG. 2. By calculating the resistor network from the equivalent circuit for the body impedances of the patient shown in FIG. 1, the five bioimpedance curves for the individual body segments of the patient's arms and legs can for example be determined (FIG. 2 right). By this means—on the one hand by redundancy, and on the other by signal analysis methods—the susceptibility to interference can be reduced and greater accuracy of measurement achieved, while more informative evaluations at the level of individual body segments can be carried out. For this reason the above-mentioned arrangement with eight electrodes is preferably employed in the patient supporting device which is described below and shown in FIGS. 3 and 4.

It is also possible to allocate coupling-in and coupling-out sensors to the measurement of different parts of the body. Thus for example current can be impressed from the right hand to the left foot, and a voltage can be measured between the right and left foot. In this manner, only the bioimpedance of the right leg is determined.

The patient supporting device comprises a patient couch (1), such as is already known in principle from the prior art, with a patient support surface, whose back rest (2), head rest if any, seat (3) and leg rest (4) are adjustable to a multiplicity of positions, and with adjustable arm rests (5), and which enables the patient to adopt both sitting and lying positions.

The patient supporting device has a patient support surface which is divided into three segments (back rest (2), seat (3) and leg rest (4)). Between the individual segments there are pivot joints which are adjustable by means of motor-driven positioning apparatuses, so that the three segments can be pivoted with respect to each other to a multiplicity of positions. Further, a motor-driven adjustable head rest can also be provided, to give the patient's head more comfortable support when the patient supporting device is adjusted to a lying position. It is also possible to equip the patient supporting device with motor-driven height-adjustable arm rests (5), in order to further facilitate the influencing of the hydrostatic pressure. In addition, a lifting and pivoting unit is provided under the seat segment, by means of which the height and angle of inclination of this segment can be adjusted. This unit can optionally be operated via a manual adjusting unit (10) or controlled by the dialysis device (12).

The patient supporting device has electrode arrays (linear contact electrode arrays) as coupling-in electrodes (6a, 7a, 8a, 9a) and coupling-out electrodes (6b, 7b, 8b, 9b) which are disposed in the foot rest (13), which can be adjustable as regards its position according to the length of the patient's legs, in the area of the heel support for the patient's right and left legs, as well as in the arm rests (5) in the terminal forearm area near the carpal bones of the patient's right and left arms in the respective patient support areas on the patient supporting device. After the positioning of the patient on the patient support surface of the patient supporting device, the electrode arrays are electrically contacted by skin areas that are not covered by clothing, such electrode arrays comprising coupling-in electrodes (6a, 7a, 8a, 9a) and coupling-out electrodes (6b, 7b, 8b, 9b). In addition, straps can be provided as immobilizing means, to immobilize the patient's body if necessary such that contact is ensured during the time required for the treatment. (However, brief movements on the part of the patient resulting in temporary interruption of electrical contact do not pose a problem.) It is however also conceivable to increase the number of measurement points (=coupling-in electrodes) and dispose these in the patient support area on the patient supporting device additionally in the patient's calf area, lumbar region, neck area and elbow area; in the case of electrodes disposed laterally to the sagittal plane, the electrodes are in each case disposed symmetrically in pairs for both halves of the body.

The electrodes and/or electrode arrays can be provided with an elastically raised (or resilient) contact area, to make more certain that there is good contact with the patient's skin. Within each electrode array, only the electrode which corresponds most closely to the desired anatomical position is activated. This can be ensured for example if the patient is automatically measured (see below) and the desired positions of the electrodes are calculated from this measurement, or if electrical measurements are used to determine the best located electrodes in each case (e.g. the outermost electrode that is contacted in each case), or if for example pressure sensors measure the force bearing on the area of each electrode (integrated over a longer measurement period, in order to minimize errors due to movement artifacts), and from this for example the body height is determined, and from the body height the electrode to be used in each case.

The patient supporting device also comprises a device for determining the patient's weight, which can be automatically measured and used during the calculations, for example, of the bioimpedance measurement, and during the setting up of the dialysis device; this removes the need for a weighing done in advance and manual input of the weight. The weighing can be carried out by determining the weight of the patient support surface with the patient upon it, and subtracting from this the (known) weight of the empty patient support surface. The result of the weighing can be shown in the display of the adjusting unit (10) and/or the dialysis device (12).

In addition, a plurality of pressure sensors (11) are integrally disposed in the back rest, to enable the determination of the patient's height. Alternatively, two laser scanners are provided, mounted on an arm to the side of and above the patient, or optionally on the ceiling and walls of the treatment room, by means of which the surface of the patient's body can be scanned and captured three-dimensionally throughout the entire treatment period. From this it is possible not only to determine the patient's body height and stature or build (for example for the precise calculation of hydrostatic pressure), but also to detect breathing and movement artifacts, as well as changes in volume, for example in the area of the legs, thorax or abdomen, caused by the dialytic water removal. It is, however, also possible—and in many cases sufficient—to detect only the body height by means of the above mentioned pressure sensors, or by means of ultrasonic or laser distance measurement (by measuring the distance to the soles of the feet and the crown of the head).

The patient supporting device can also have a fingerprint sensor in the area of the armrests on which the fingers are placed, by means which the patient can be unambiguously identified, and the data set for this patient with all relevant stored information concerning the patient as well as data concerning the dialysis treatment can be automatically retrieved, for example from a PC or a hospital server.

The coupling-in electrodes (6a, 7a, 8a, 9a) are electrically connected to a measurement signal generator, whose measurement signal is coupled into the patient's body via the coupling-in electrodes. The coupling-out electrodes (6b, 7b, 8b, 9b)—by means of which the electrical measurement value generated in the patient's body by the coupled-in measurement signal (an impressed measurement current frequency-modulated in the frequency range of for example 1 kHz to 1 MHz) is coupled out—are electrically connected to a detecting apparatus, by means of which the coupled-out electrical measurement value is detected and processed, by means of evaluation and calculation over the frequency range, by the evaluation apparatus (which is independent (10) or integrated in the dialysis device (12)).

In this way it is possible to determine for example the hydration status of the patient and the excess body water that is to be removed by dialysis. This information can be transmitted to the dialysis device (12) via a suitable interface for connecting the dialysis device (12), which in turn can make use of this information, for example to adjust the transmembrane pressure in the dialysis chamber of the dialyzer, by corresponding control of the blood pumps, dialysate pumps or ultrafiltration pumps of the dialysis device (12).

LIST OF REFERENCE SIGNS 1 patient couch
2 back rest
3 seat
4 leg rest
5 arm rest
6a, 6b electrodes, right hand
7a, 7b electrodes, left hand
8a, 8b electrodes, right foot
9a, 9b electrodes, left foot
10 display and operating device for position setting and bioimpedance measurement
11 pressure sensors
12 dialysis device
13 foot rest

The invention claimed is:

1. Patient support comprising
   a) an electricity conducting apparatus for carrying out a bioimpedance measurement on a patient's body, wherein the apparatus comprises
      a signal carrying device for coupling a measurement signal into the patient's body and
      an electrically conductive device for coupling an electrical measurement value thereby generated in the patient's body out of the patient's body,
   b) an apparatus for at least one of detection and calculation of hydrostatic pressure at least by inclination of one or more position adjustment parameters of the patient support selected from the group consisting of a back rest, leg rest, and foot rest, and
   c) a data carrying interface for connecting to a medical treatment device,
   wherein, when connected to the medical treatment device via the interface, data correlated with the electrical measurement value transmitted via the interface to the medical treatment device at least one of controls and regulates the medical treatment device.

2. Patient support according to claim 1, characterized in that the medical treatment device is a dialysis device.

3. Patient support according to claim 1, characterized in that the apparatus for carrying out a bioimpedance measurement further comprises a device for determining the patient's weight.

4. Patient support according to claim 1, characterized in that the apparatus for carrying out a bioimpedance measurement further comprises at least two coupling-in electrodes, for contacting the patient's body for coupling the measurement signal into the patient's body by impressing a measurement current into the patient's body, and at least two coupling-out electrodes, for contacting the patient's body for coupling the electrical measurement value generated by the measurement signal in the patient's body out of the patient's body by capturing a change in potential generated by the measurement signal in the patient's body.

5. Patient support according to claim 4, characterized in that at least one coupling-in electrode and at least one coupling-out electrode are for contacting each arm and each leg of the patient for carrying out a segmental bioimpedance measurement.

6. Patient support according to claim 1, characterized in that the bioimpedance measurement is at least one of bioimpedance spectroscopy and bioimpedance vector analysis, with selective and specific detection of amplitude variation and phase displacement in the electrical measurement value.

7. Patient support according to claim 1, characterized in that the bioimpedance measurement comprises at least one of a linear and a non-linear analysis of the electrical measurement value.

8. Patient support according to claim 2, characterized in that, when connected to the medical treatment device, the electrical measurement value of the bioimpedance measurement in the patient's body is evaluated together with a blood analysis in an extracorporeal circulation of the dialysis device.

9. Patient support according to claim 1 further comprising a device for determining the patient's height containing at least one of pressure sensors and pressure sensor arrays disposed in the area of patient supporting surfaces of the patient support.

10. Patient support according to claim 1 further comprising an optical measurement device for three-dimensional detection of the patient's measurements.

11. Patient support according to claim 1 further comprising arm rests and a detecting apparatus for detecting positions of the arm rests.

12. Patient support according to claim 1 further comprising a motor-driven adjusting device for adjusting at least one of the back rest, leg rest, and foot rest.

13. Patient support according to claim 12, characterized in that the motor-driven adjusting device is controlled by the medical treatment device.

14. Patient support according to claim 1 further comprising a device for determining the patient's identity.

15. Treatment apparatus comprising
   a patient support according to claim 1,
   the medical treatment device, and
   a bioimpedance evaluation apparatus for evaluating the bioimpedance from the electrical measurement value that is coupled out by the electricity conducting apparatus for carrying out a bioimpedance measurement,
   wherein the medical treatment device is at least one of controlled and regulated by the bioimpedance.

16. Patient support according to claim 1 further comprising a fingerprint sensor.

* * * * *